(12) United States Patent
Belliard

(10) Patent No.: US 8,663,283 B2
(45) Date of Patent: Mar. 4, 2014

(54) SYSTEM FOR STABILIZING AT LEAST TWO VERTEBRAE

(75) Inventor: Karl Pierre Belliard, La Membrolle (FR)

(73) Assignee: Zimmer Spine S.A.S., Cite Mondiale, Bordeaux (FR)

( * ) Notice: Subject to any disclaimer, the term of this patent is extended or adjusted under 35 U.S.C. 154(b) by 703 days.

(21) Appl. No.: 12/469,414

(22) Filed: May 20, 2009

(65) Prior Publication Data

US 2009/0292317 A1 Nov. 26, 2009

(30) Foreign Application Priority Data

May 20, 2008 (EP) ..................................... 08305183

(51) Int. Cl.
*A61B 17/70* (2006.01)

(52) U.S. Cl.
USPC ........................................... 606/249; 606/248

(58) Field of Classification Search
USPC ................................................ 606/246–279
See application file for complete search history.

(56) References Cited

U.S. PATENT DOCUMENTS

| | | | |
|---|---|---|---|
| 902,040 A | 10/1908 | Wychoff | |
| 1,346,940 A | 7/1920 | Collins | |
| 2,049,361 A | 7/1936 | Ericsson | |
| 5,030,220 A | 7/1991 | Howland | |
| 5,356,412 A | 10/1994 | Golds et al. | |
| 5,413,576 A | 5/1995 | Rivard | |
| 5,609,634 A | 3/1997 | Voydeville | |
| 5,667,508 A | 9/1997 | Errico | |
| 5,702,399 A | 12/1997 | Kilpela et al. | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |

(Continued)

FOREIGN PATENT DOCUMENTS

| | | |
|---|---|---|
| DE | 19716504 | 12/1998 |
| EP | 0780096 | 6/1997 |

(Continued)

OTHER PUBLICATIONS

European Search Report for EP 08305124.3, dated Oct. 20, 2008, 3 pages.

(Continued)

*Primary Examiner* — Jerry Cumberledge
*Assistant Examiner* — Nicholas Plionis
(74) *Attorney, Agent, or Firm* — Seager Tufte & Wickhem LLC

(57) ABSTRACT

This disclosure provides a spinal stabilization system and method for stabilizing at least two vertebrae. The system holds together the vertebrae while allowing a limited amount of relative movement between the vertebrae. The system may include a flexible braid having two free ends, at least one spacer interposed between the spinous processes of the vertebrae, and a securing mechanism for securing the two ends of the braid to hold the at least one spacer between the spinous processes of the vertebrae. In some embodiments, the securing mechanism may comprise parts movable relative to each other. Portions of the braid may be placed between the movable parts. A mechanical member may cause the movable parts to move towards each other to secure the two ends of the braid.

10 Claims, 10 Drawing Sheets

(56) References Cited

U.S. PATENT DOCUMENTS

| | | |
|---|---|---|
| 6,179,838 B1 | 1/2001 | Fiz |
| 6,391,030 B1 | 5/2002 | Wagner et al. |
| 6,478,798 B1 | 11/2002 | Howland |
| 6,514,255 B1 | 2/2003 | Ferree |
| 6,547,770 B2 | 4/2003 | Carlsson et al. |
| 6,569,164 B1 | 5/2003 | Assaker et al. |
| 6,616,669 B2 | 9/2003 | Ogilvie et al. |
| 6,682,533 B1 | 1/2004 | Dinsdale et al. |
| 6,946,000 B2 | 9/2005 | Senegas et al. |
| 2002/0116013 A1 | 8/2002 | Gleason et al. |
| 2004/0097942 A1 | 5/2004 | Allen et al. |
| 2004/0138666 A1 | 7/2004 | Molz, IV et al. |
| 2004/0249379 A1* | 12/2004 | Winslow et al. ............ 606/61 |
| 2005/0085815 A1 | 4/2005 | Harms |
| 2005/0273983 A1 | 12/2005 | Mattchen |
| 2006/0064166 A1* | 3/2006 | Zucherman et al. ....... 623/17.11 |
| 2006/0084985 A1* | 4/2006 | Kim ............................ 606/61 |
| 2006/0235387 A1 | 10/2006 | Peterman |
| 2006/0235391 A1 | 10/2006 | Sutterlin |
| 2007/0299445 A1 | 12/2007 | Shadduck et al. |
| 2008/0033556 A1* | 2/2008 | Le Couedic et al. ...... 623/17.16 |
| 2008/0033557 A1 | 2/2008 | Pasquet et al. |
| 2008/0114357 A1* | 5/2008 | Allard et al. .................. 606/61 |
| 2008/0125780 A1 | 5/2008 | Ferree |
| 2008/0208256 A1 | 8/2008 | Thramann |

FOREIGN PATENT DOCUMENTS

| | | | |
|---|---|---|---|
| EP | 1815812 | | 8/2007 |
| FR | 522040 | | 7/1921 |
| FR | 26156 | | 9/1932 |
| FR | 2704745 | | 11/1994 |
| FR | 2704745 | A1 | 11/1994 |
| FR | 2722088 | | 1/1996 |
| FR | 2722088 | A1 | 1/1996 |
| FR | 2799948 | A1 | 4/2001 |
| FR | 2817929 | | 6/2002 |
| FR | 2867057 | | 9/2005 |
| FR | 2870718 | | 12/2005 |
| FR | 2890850 | | 3/2007 |
| FR | 2890851 | | 3/2007 |
| FR | 2897771 | A1 | 8/2007 |
| GB | 2269753 | A | 2/1994 |
| JP | 2001299770 | | 10/2001 |
| WO | WO9416635 | A1 | 8/1994 |
| WO | WO0209604 | A1 | 2/2002 |
| WO | WO0217803 | A2 | 3/2002 |
| WO | WO 02051326 | A1 | 7/2002 |
| WO | WO 02071960 | A1 | 9/2002 |
| WO | WO 2003007829 | A1 | 1/2003 |
| WO | WO03103519 | A1 | 12/2003 |
| WO | WO 03103519 | A2 | 12/2003 |
| WO | WO2004010881 | A1 | 2/2004 |
| WO | WO 2005020860 | A3 | 3/2005 |
| WO | WO 2005120277 | A1 | 12/2005 |
| WO | WO2006034423 | A2 | 3/2006 |
| WO | 2006106246 | A2 | 10/2006 |
| WO | WO 2006106268 | A3 | 10/2006 |
| WO | WO2006106246 | | 12/2006 |
| WO | WO 2007023240 | A3 | 3/2007 |
| WO | WO 2007034112 | A1 | 3/2007 |
| WO | WO2007036657 | | 4/2007 |
| WO | WO 2007099258 | A2 | 9/2007 |
| WO | WO 2007120177 | A2 | 10/2007 |
| WO | WO 2008051802 | A2 * | 5/2008 |
| WO | WO2009130276 | A1 | 10/2009 |
| WO | WO2009141393 | A1 | 11/2009 |

OTHER PUBLICATIONS

English Translation of International Preliminary Report for PCT/FR2006/050898 on Patentability Chapter I, dated Apr. 29, 2008, 6 pages.
English Translation of International Preliminary Report on Patentability Chapter I for PCT/FR2006/050909, dated Apr. 8, 2008, 5 pages.
English Translation of the Written Opinion of the International Search Authority for PCT/FR2006/050909, dated Apr. 2, 2008, 4 pages.
English Translation of the Written Opinion of the International Search Authority for PCT/FR2006/050898, dated Apr. 28, 2008, 5 pages.
European Search Report for EP 08305183, dated Mar. 19, 2009, 10 pages.
European Search Report for EP 08305326, dated Nov. 12, 2008, 3 pages.
European Search Report for EP 2052689, dated Apr. 15, 2008, 6 pages.
French Preliminary Search Report and Written Opinion for FR200650609, dated Jun. 30, 2006, 5 pages.
International Search Report for WO2009053423, dated May 19, 2009, 4 pages.
International Search Report mailed Nov. 24, 2008 for PCT/EP2008/063682, 3 pages.
International Search Report for PCT/FR2006/050909 published as WO/2007/034112, dated Jan. 24, 2007, 3 pages.
Office Action for U.S. Appl. No. 10/521,914, dated Dec. 29, 2006, 21 pages.
Office Action for U.S. Appl. No. 10/521,914, dated Mar. 19, 2008, 7 pages.
Office Action for U.S. Appl. No. 10/521,914, dated Jun. 16, 2006, 13 pages.
Office Action for U.S. Appl. No. 10/521,914, dated Jul. 30, 2007, 13 pages.
International Search Report and Written Opinion for PCT/US2009/038977 mailed Jul. 22, 2009, 13 pages.
Korean Examination report for Korean Patent Application No. 1020057001238, mailed Feb. 23, 2010, 3 pages.
French Preliminary Search Report for FR0209317, dated Apr. 9, 2003, 1 page.
French Preliminary Search Report for FR0509629 mailed Jun. 9, 2006, 2 pages.
International Search Report for FR200302307, dated Jan. 2, 2004, 2 pages.
Australian Search Report for Australian Patent Application No. 2003267529, dated Nov. 15, 2007, 2 pages.
French Preliminary Search Report FR0509570, dated Jun. 29, 2006, 2 pages.
International Search Report for PCT/FR2006/050898, dated Feb. 2, 2007, 2 pages.
Written Opinion for PCT/US2009/038977, mailed Feb. 24, 2010, 7 pages.
European Search Report for European Patent Application No. 07 301 454.0, mailed Sep. 25, 2008, 8 pages.
International Search Report and Written Opinion for PCT Application No. PCT/EP2008/062791, completed Nov. 18, 2008, mailed Dec. 4, 2008, 10 pages.
French Preliminary Search Report for French Application No. 0757814, issued May 22, 2008, 2 pgs.
International Preliminary Report on Patentability issued in International Patent Application No. PCT/EP2008/062791, Mar. 30, 2010, 7 pages.
French Preliminary Search Report in French Patent Application No. FR 0405611, dated Jan. 12, 2005, 2 pages.
European Search Report issued in EP 08305326 on Nov. 25, 2006, Abbott Spine, 3 pages.

\* cited by examiner

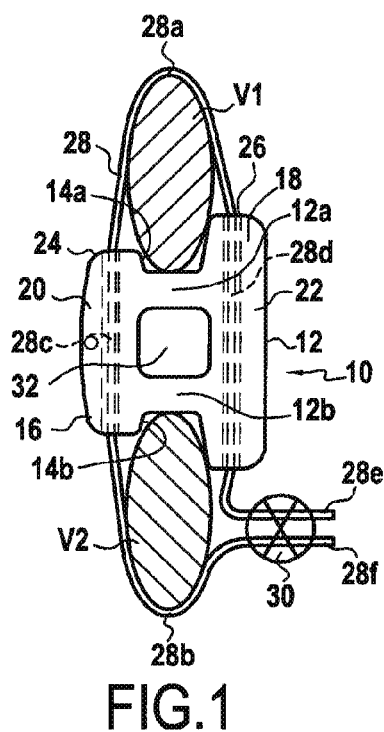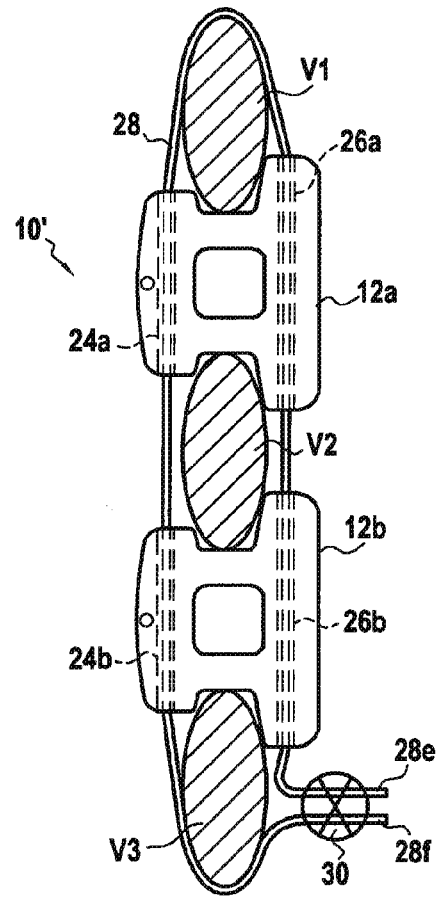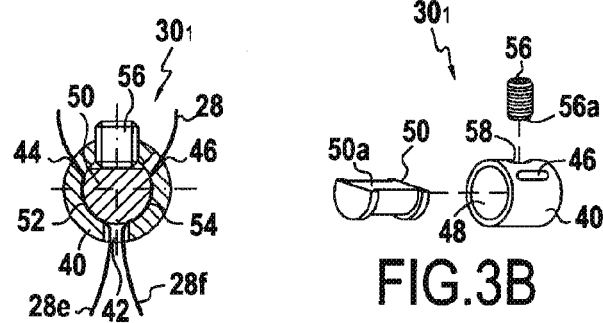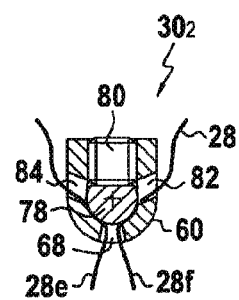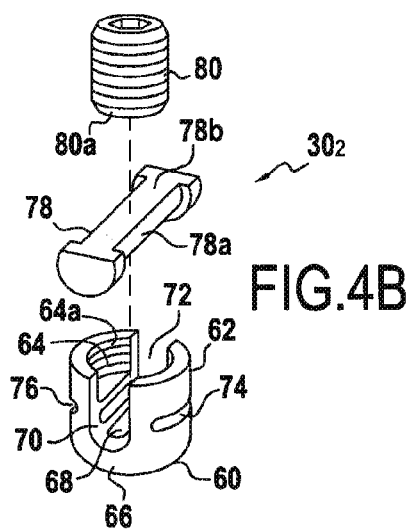

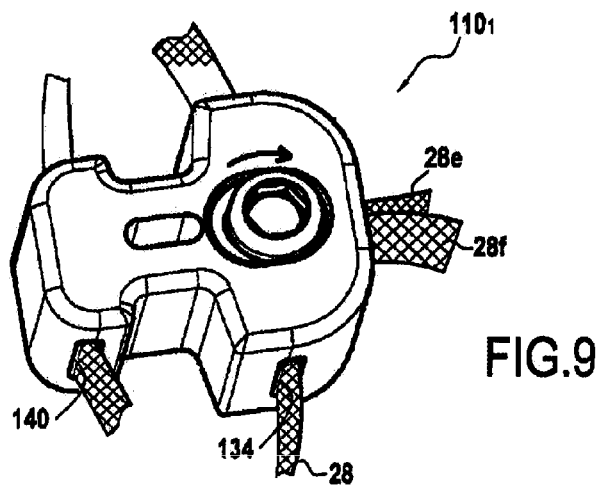
FIG. 9
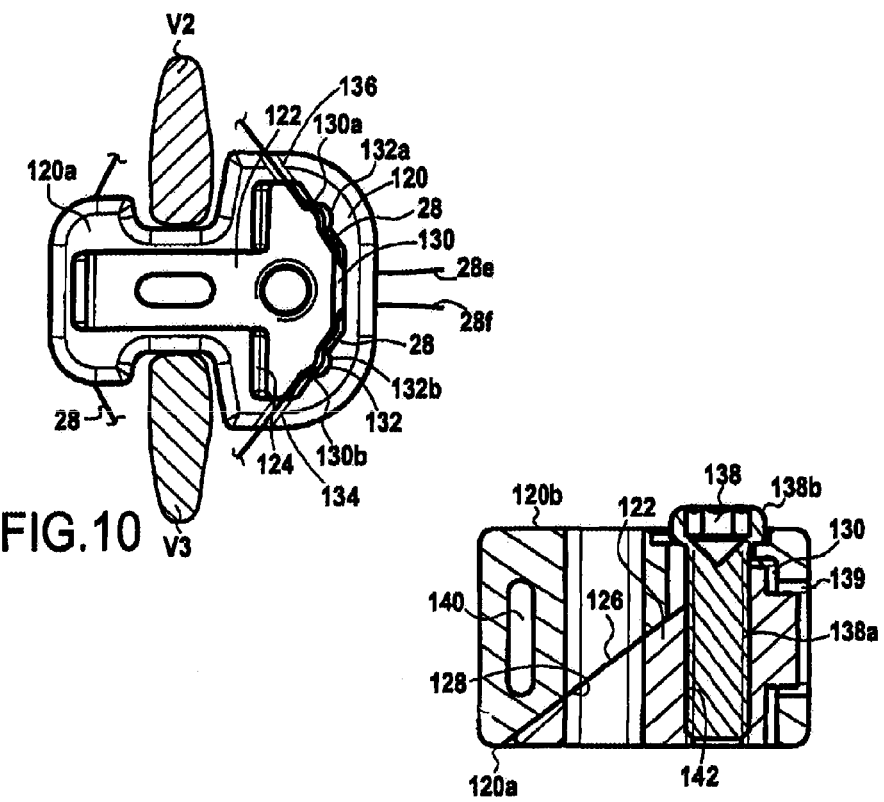
FIG. 10
FIG. 10A

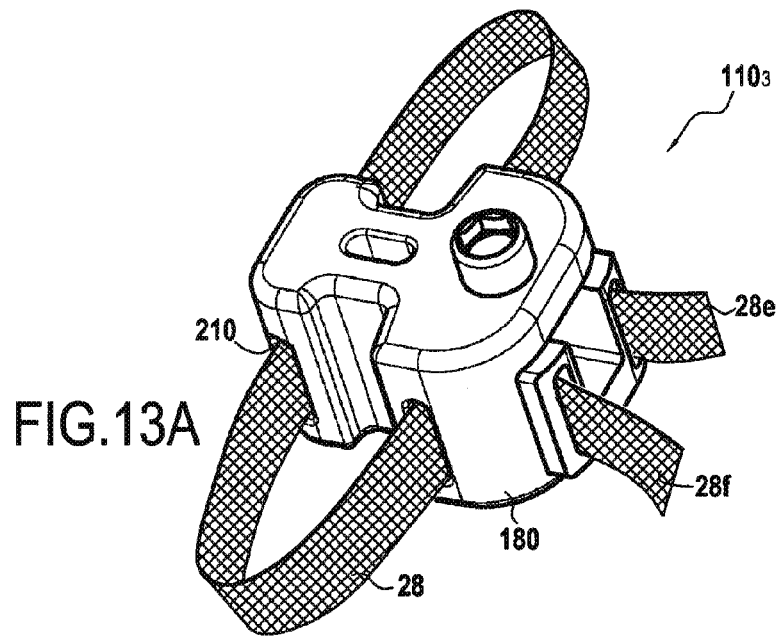
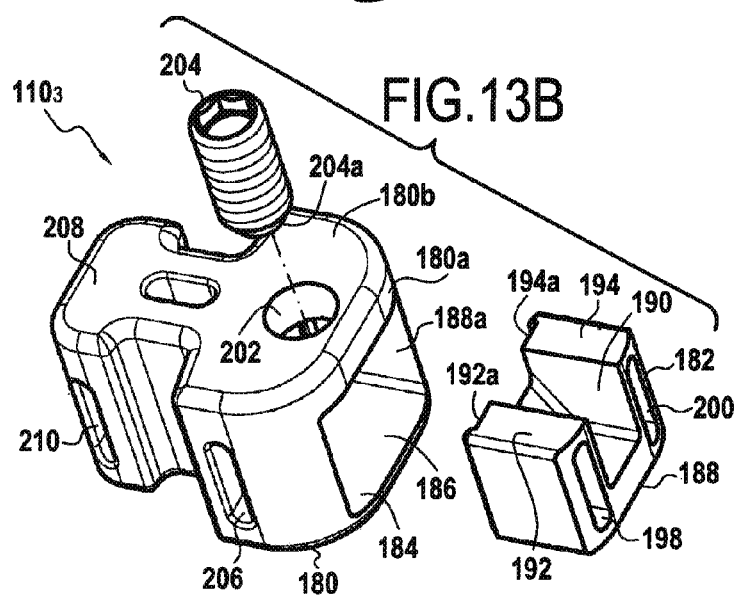
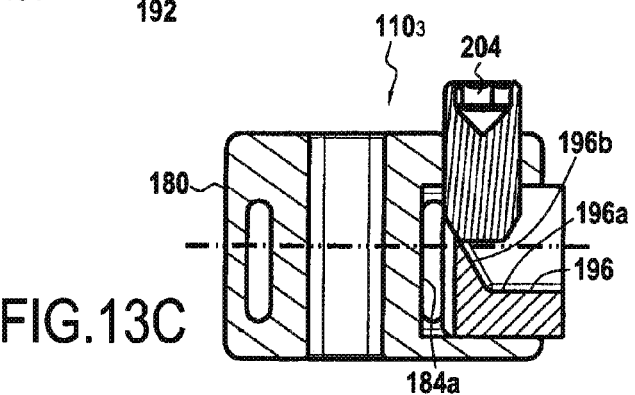

SYSTEM FOR STABILIZING AT LEAST TWO VERTEBRAE

CROSS-REFERENCE TO RELATED APPLICATIONS

This application claims a benefit of priority under 35 U.S.C. 119(a) of the filing date of European Patent Application No. 08305183, filed May 20, 2008, entitled "SYSTEM FOR STABILIZING AT LEAST TWO VERTEBRAE," which is fully incorporated herein by reference.

TECHNICAL FIELD OF THE DISCLOSURE

The present disclosure relates to a system and method for stabilizing at least two vertebrae, including but not limited to dynamic stabilization.

BACKGROUND OF THE RELATED ART

With certain pathologies of the vertebral column, the surgeon might need to perform surgery for securing at least two vertebrae to each other. Sometimes, the surgeon will need to secure a larger number of vertebrae to one another, e.g., 3 or 4.

In order to perform this operation, when it is desired to stabilize only two vertebrae, it is known to place between them an intervertebral implant constituted by a spacer that is usually disposed between the spinous processes of the vertebrae, together with securing means such as braids or ties that surround the spinous processes in order to hold the spacer between the vertebrae. For that purpose, in addition to the spacer, it is known to use a braid that presents two free ends that are secured to the spacer, e.g., with the help of a self-locking system of the type described in PCT patent application WO 2005/120277. Nevertheless, making such a spacer with usually releasable locking means presents certain drawbacks.

SUMMARY OF THE DISCLOSURE

A first object of the present disclosure is to provide a stabilization system that is dynamic, i.e., a system that, while holding together at least two vertebrae, nevertheless allows a limited amount of relative movement between these two vertebrae.

Another object of the disclosure is to provide such a system that enables the surgeon to exert the required amount of traction on the free ends of the braid system under improved conditions, and regardless of the number of vertebrae that are to be stabilized.

To achieve these objects, according to the present disclosure, there is provided a system for stabilizing at least two vertebrae, the system comprising:
- a flexible braid having two ends and a length defined by the two ends, the length of the flexible braid forming a single loop around spinous processes of the at least two vertebrae;
- at least one spacer interposed between the spinous processes of the two vertebrae and the single loop of the flexible braid, the spacer including a body and elements for engaging portions of the single loop of the flexible braid; and
- a securing mechanism for securing the two ends of the flexible braid to hold the at least one spacer between the spinous processes of the two vertebrae.

Because the system has at least one spacer, if the stabilization system involves only two vertebrae, then only one spacer is used and the securing mechanism for securing the two free ends of the braid is a component that is distinct from the spacer.

In addition, regardless of whether the braid system has one or more braids, since it forms a single loop around the spinous processes of the vertebrae to be stabilized, having functionally only two free ends suitable for achieving traction, the surgeon can easily exert said traction.

In addition, regardless of whether the braid system has one or more braids, since it is flexible and possibly presents a certain amount of elasticity, a limited amount of relative movement remains possible between the vertebrae even after the surgeon has exerted traction on the free ends of the braid system is an amount appropriate to obtain the desired stabilization.

In a first embodiment of the stabilization system, the braid system has only one braid, the co-operating elements of the spacer merely comprising means for guiding the braid, and the securing mechanism for securing the free ends of the braid is distinct from the spacers.

An advantage of this embodiment is that all of the spacers can be identical. In some embodiments, the spacers can have a simple construction.

In a second embodiment of the stabilization system, the braid system comprises only one braid, and a securing mechanism for securing the two free ends of the braids is secured to one of the spacers.

The securing mechanism for securing the free ends of the braid may form an integral portion of the spacer to which it is secured, or it may be removably mounted thereon.

In this second embodiment, the spacers that do not have a securing mechanism need only include elements for guiding portions of the braid, or they may include elements for clamping to a portion of the braid, or indeed both types may be involved.

In a third embodiment, the stabilization system has two braids, the body of one of the spacers having two side faces, the securing mechanism comprising a first securing member secured to a first side face and a second securing member secured to a second side face, each braid presenting a first end permanently secured to the body of said spacer and a second end that is free, suitable for receiving traction, and retractably secured to one of the securing members.

In all of the above-defined embodiments, one or more braids or ties are used and that the braid may be made of a material that is flexible, or possibly elastic, so that the braid allows a limited amount of relative movement to the two or more vertebrae while providing a stabilizing effect.

In addition, regardless of whether there is only braid or more, the braid system may form a single loop passing, directly or indirectly, around the spinous processes of the set of vertebrae for stabilizing. This single loop functionally presents only two free ends, on which it is easy for the surgeon to exert traction.

Under certain circumstances, the braid system may physically present two pairs of free ends. Nevertheless, functionally, traction is exerted by the surgeon on only one of the pairs of free ends of the braid system. The surgeon can then select the pair of free ends that is easier to access.

BRIEF DESCRIPTION OF THE DRAWINGS

Other characteristics and advantages of the disclosure are described below. The following description provides examples of several embodiments. The description refers to the accompanying figures, in which:

FIG. 1 is an elevation view of one embodiment of a stabilization system for two vertebrae, using an embodiment of a securing mechanism for securing the free ends of a braid;

FIG. 2 is an elevation view of one embodiment of a stabilization system for three vertebrae, using two spacers and the securing mechanism of FIG. 1;

FIG. 3A is a cross-sectional view of an embodiment of a securing mechanism for securing the ends of a braid;

FIG. 3B is an exploded perspective view of the securing mechanism of FIG. 3A;

FIG. 4A is a cross-sectional view of a second embodiment of a securing mechanism for securing the ends of the braid;

FIG. 4B is an exploded perspective view of the securing mechanism of FIG. 4A;

FIG. 9 is a perspective view of a spacer provided with a first type of braid-securing mechanism;

FIG. 10 is a view of the underside of the spacer in FIG. 9 positioned between two vertebrae;

FIG. 10A is a cross-sectional view along the length of the spacer in FIG. 9, showing a movable part;

FIG. 13A is a perspective view of a third embodiment of a spacer fitted with a braid-securing mechanism;

FIG. 13B is an exploded view of the spacer shown in FIG. 13A;

FIG. 13C is a cross-sectional view along the length of the spacer in FIG. 13A, showing a movable part;

DETAILED DESCRIPTION

Figure 5:
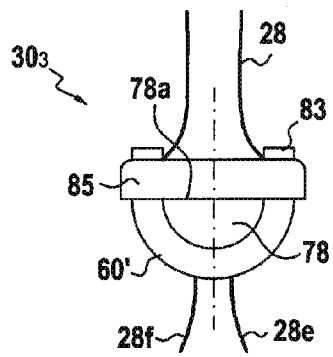
FIG. 5 is a vertical section view of a third embodiment of a securing mechanism for securing the ends of the braid.

With reference initially to FIGS. 1 and 2, there follows a description of a first embodiment of the stabilization system of the disclosure. FIG. 1 shows a stabilization system 10 for stabilizing two vertebrae V1 and V2, FIG. 2 showing a similar stabilization system 10' for stabilizing three vertebrae V1, V2, and V3.

In this first embodiment, use is made solely of intervertebral spacers that are simple, i.e., spacers that do not include their own securing mechanism for securing the free ends of the braid on the spacer, with there being only one braid.

More precisely, in FIG. 1, the stabilization system 10 has a simple intervertebral spacer 12 with ends 12a and 12b provided with recesses 14a and 14b for receiving the spinous processes of the vertebrae V1 and V2. Preferably, the distal prongs 16 defining the recesses 14a and 14b are much smaller in height than are the proximal prongs 18 that also define the same recesses. As is known, this asymmetry of the prongs makes it possible to use a lateral approach for putting the spacer into place between the processes of the vertebrae V1 and V2 (see PCT patent application WO 2007/099258, which is incorporated herein by reference). The lateral portions 20 and 22 of the spacer that terminate in the prongs 16 and 18 are provided with passages 24, 26 that extend over their full length so as to allow a securing tie or braid 28 to pass freely. The braid 28 is made of a material that confers a certain amount of flexibility thereto and possibly also a certain amount of elasticity in order to obtain the desired dynamic stabilization effect as mentioned above. The braid 28 has portions 28a, 28b that pass around the spinous processes of the vertebrae V1 and V2 in part, intermediate portions 28c and 28d that are engaged in the passages 24 and 26, and two free ends 28e and 28f. The ends 28e and 28f of the braid 28 are secured to each other by a securing mechanism 30 represented symbolically in FIG. 1. This braid-securing mechanism is described in greater detail below.

It should be understood that the structure of the simple spacer 12 is very simple, since it does not itself include any braid-securing mechanism. To provide dynamic stabilization for dynamically stabilizing the vertebrae V1 and V2, it is possible to have a hollow 32 in the central portion of the body of the spacer, thereby giving it a certain amount of elasticity or a certain amount of deformability that is additional to the flexibility of the braid 28. In addition, as explained below, when putting the stabilization system into place, the surgeon can exert appropriate traction on the ends 28e and 28f, with the help of a traction instrument that is itself known, so as to find a compromise between the desired stabilization and the desired possibility of relative movement between the vertebrae in order to obtain the dynamic stabilization effect. Such a traction instrument is described in particular in PCT patent application WO 2007/034112, which is incorporated herein by reference.

FIG. 2 shows a system for stabilizing three vertebrae that is very similar to the system shown in FIG. 1. The only difference lies in the fact that two simple spacers 12a and 12b are interposed between the spinous processes of vertebrae V1, V2, and V3. The braid 28 is itself identical to that of FIG. 1, but longer, passing around portions of the spinous processes of vertebrae V1 and V3, and passing freely within the internal passages 24a, 26a, and 24b, 26b of the simple spacers 12a and 12b. As in FIG. 1, the ends 28a and 28f are secured to each other by a securing mechanism 30 that may be identical to that of FIG. 1, and that is described below.

It should be understood that the embodiment shown in FIG. 2 enables three vertebrae to be stabilized with the help of intervertebral spacers of a structure that is very simple, since none of them includes any means for securing a braid. It is possible to provide a system of the type shown in FIG. 2 for stabilizing more than three vertebrae, by providing a corresponding number of simple spacers. As in the embodiment of FIG. 1, the tension in the braid 28 can be adjusted prior to locking the braid in place with the securing mechanism 30.

It should be understood that in this first embodiment, the spacers act relative to the braid 28 solely to provide guidance, as is achieved by the various internal passages 24, 26, 24a, 24b, 26a, 26b.

With reference to FIGS. 3A to 6, there follows a description of several embodiments of a securing mechanism for securing the ends of the braid 28, which is given overall reference 30 in FIGS. 1 and 2.

In the first embodiment, the securing mechanism $30_1$, as shown in FIGS. 3A and 3B, essentially comprises a cylindrical sleeve 40 having a first slot 42 to allow the free ends 28e and 28f of the braid 28 to pass therethrough, and second and third slots 44 and 4 in its sides also to allow the braid 28 to pass through, after it has passed through the cylindrical housing 48 defined by the sleeve 40. A locking part 50 of substantially semicylindrical shape can be inserted in the cylindrical housing 48 of the sleeve 40 so that portions 52 and 54 of the braid 28 are interposed between the inside wall of the cylindrical housing 48 and the outside face of the semicylindrical part 50. The securing mechanism $30_1$ also including a clamping screw 56 capable of co-operating with a tapped orifice 58 formed in the cylindrical sleeve 40 in a position diametrically opposite to the first slot 42. When the screw 56 is engaged in the tapped orifice 58, its end 56a comes to bear against the top face 50a of the part 50, thereby providing claiming by wedging the braid portions 52 and 54 between the part 50 and the wall of the housing 48. By exerting appropriate traction on the free ends 28e and 28f of the braid 28 before tightening the screw 56, the surgeon can obtain suitable tension in the braid 28 when it passes around the spinous processes of the vertebrae that are to be stabilized in dynamic manner, thereby adjusting of the dynamic stabilization effect, in part.

With reference now to FIGS. 4A and 4B, there follows a description of a second embodiment $30_2$ of the securing mechanism for securing the ends of the braid.

In this embodiment, the securing mechanism comprises a body 60 presenting a side wall 62 defining a cylindrical inside housing 64 and an end wall 66. The end wall 66 is provided with a slot 68 for passing the free ends 28e and 28f of the braid 28 going towards the vertebrae. The side wall 62 of the body 60 is subdivided into two portions by diametrically opposite notches 70 and 72. Finally, the side wall of the body 62 is provided with two side slots 7 4 and 76 for passing braid portions 28 going towards the vertebrae. The braid-securing mechanism also includes a locking part 78 of generally semicylindrical shape that can be put into place in the inside housing 64, projecting through the notches 70 and 72. Finally, the securing mechanism $30_2$ includes a screw 80 that can co-operate with tapping 64a formed in the inside portion of the housing 64. As shown better in FIG. 4A, portions 82 and 84 of the braid 28 are disposed between the inside wall of the end 66 of the body 60 and the side face 78a of the locking part 78. By tightening the screw 80 in the taping 64a, the end 80a of the screw 80 comes to bear against the top face 78b of the locking part 78. Thus, by tightening the screw 80, the surgeon can secure the braid 28 by wedging it between the locking part 78 and the inside face of the body 60.

FIG. 5 shows a third embodiment of the braid-securing mechanism $30_3$. This embodiment is similar to that of FIGS. 4A and 4B. It comprises a body 60' that is identical to the body 60 of the securing mechanism $30_2$ except that it does not have the side slots 74 and 76, and the top portion of its outside face is provided with a thread 83. The clamping screw 80 is replaced by a tapped ring 85 that co-operates with the thread 84 of the body 60'. By tightening the tapped ring 85, the side wall of the body 60' is deformed elastically, thereby securing portions of the braid 28 by wedging them, this securing effect being accompanied by the action of the tapped ring 85 against the ends of the top face 78a of the locking part 78.

Figure 6:
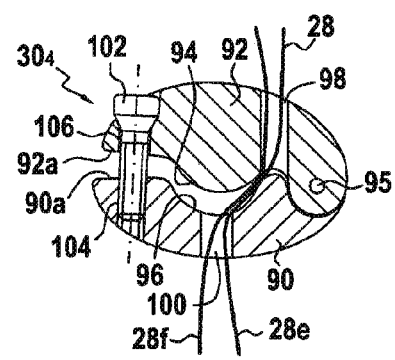
FIG. 6 is a cross-sectional view of a fourth embodiment of a securing mechanism for securing the ends of the braid.

FIG. 6 shows a fourth embodiment of the braid-securing mechanism $30_4$. The securing mechanism $30_4$ is constituted by two jaws 90 and 92 that are hinged relative to each other at a first end about an axis 95. The facing faces 92a and 90a of the jaws 90 and 92 have shapes that are complementary, and in particular that define a substantially semicylindrical convex portion 94 and a substantially semicylindrical concave portion 96. The jaw 92 is provided with a slot 98 for passing the braid 28, and the jaw 90 is also provided with a slot 100 for passing the free ends 28e and 28f of the braid 28.

Thus, the braid 28 passing through the slots 98 and 100 is to be found between the complementary semicylindrical surfaces 94 and 96 of the two jaws. A locking screw 102 co-operates with a tapped orifice 104 and a smooth orifice 106 formed in the second ends of the jaws 90 and 92 respectively. By tightening the screw 102, the two jaws are caused to move towards each other and the wedge portions are secured by being wedged between the complementary surfaces 94 and 96 of the two jaws.

It would also be possible to use other systems for securing the ends of the braid, providing, in this embodiment, they are distinct from the simple spacers that are used and providing that they enable the surgeon to exert traction on the ends 28e and 28f of the braid 28 so as to obtain the desired traction.

Whatever the type of securing mechanism used, the stabilization system can be put into place via a lateral approach. Consequently, the spacers 110, 114, and 116 need to be of an appropriate shape. More precisely, the transverse height of the distal end of each spacer is smaller, while the transverse height of the proximal end of each spacer is larger, since it does not need to be capable of being inserted between the vertebrae.

Figure 7:
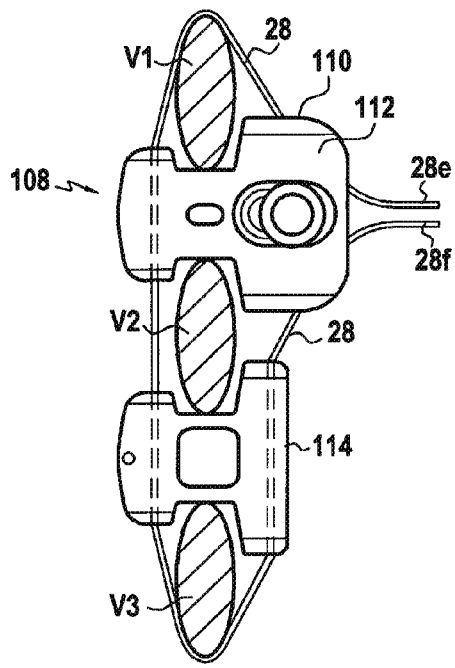
FIG. 7 is an elevation view of a system for stabilizing three vertebrae, having a simple spacer and a spacer with a braid-securing mechanism.
Figure 8:
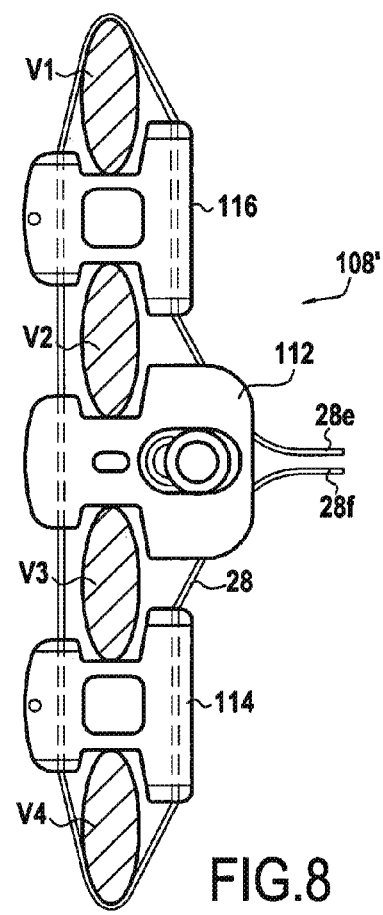
FIG. 8 is an elevation view of a system for stabilizing four vertebrae, using two simple spacers and a spacer with a braid-securing mechanism.
Figure 11:
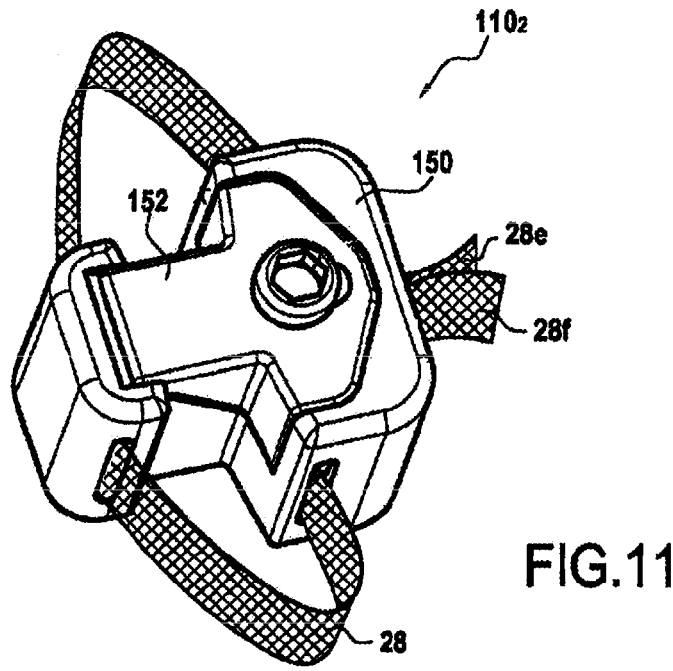
FIG. 11 is a perspective view of a second embodiment of a spacer fitted with a braid-securing mechanism suitable for use in the stabilization system of the disclosure.
Figures 12B, 12C:
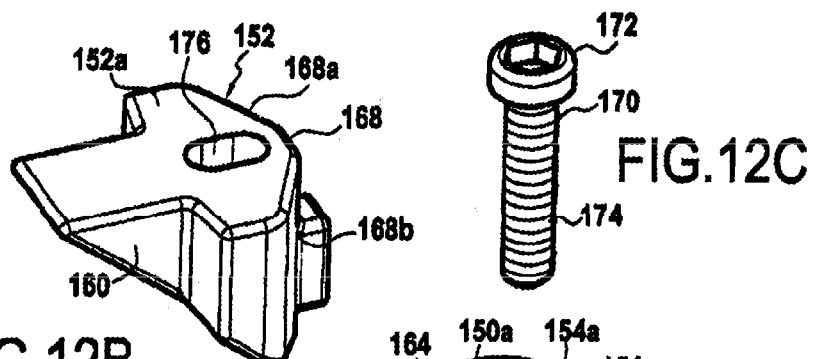
FIGS. 12A, 12B, and 12C show the various component parts of the spacer shown in FIG. 11.
Figure 12A:
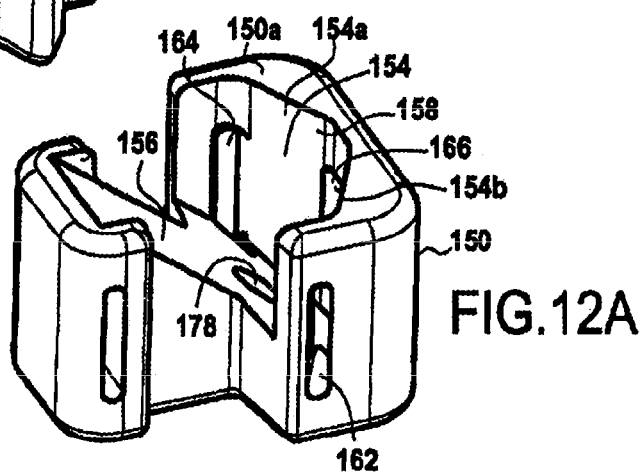

FIGS. 7 and 8 show a second embodiment of the stabilization system which involves, in FIG. 7, stabilizing three vertebrae V1, V2, and V3, and in FIG. 8, stabilizing four vertebrae V1, V2, V3, and V4.

This second embodiment differs from that described with reference to FIGS. 1 and 2 essentially by the fact that the securing mechanism for securing the free ends 28e and 28f of the braid 28 is mounted on or forms an integral part of one of the spacers interposed between the vertebrae V1, V2, and V3. In FIG. 7, there can be seen the intervertebral spacer 110 that has its own system for clamping and securing the ends of the braid, which system is described below, together with a simple spacer 114 that is identical to the simple spacers as described above. In this embodiment, the braid 28 surrounds the spinous processes of the end vertebrae V1 and V3 and passes freely along the internal passages in the simple spacer 114. The braid 28 shown in this figures has the same properties as the braid shown in FIGS. 1 and 2 for providing stabilization.

In FIG. 8, in addition to the intervertebral spacer 112 and the simple spacer 114, there is a second simple spacer 116 interposed between the spinous processes of vertebrae V1 and V2. The simple spacer 116 is identical to the simple spacer 114.

The second embodiment of the disclosure shown in FIGS. 7 and 8 presents all of the advantages of the embodiments described with reference in particular to FIGS. 1 and 2, and in particular it is possible to insert the intervertebral spacers using a lateral approach and it is possible to exert traction laterally on the ends of the securing braid 28.

In the embodiments shown in FIGS. 7 and 8, the simple spacers 114 and 116 merely perform a function of guiding the braid 28.

With reference now to FIGS. 9, 10, and 10A, there follows a description of a first embodiment $110_1$ of the spacer 112 incorporating the securing element.

In this embodiment, the securing mechanism for securing the ends of the braid forms an integral portion of the spacer $110_1$. The locking system is constituted by a stationary portion formed by the body 120 of the spacer $110_1$, and by a movable or movable portion 122. The various spacer embodiments $110_1$, $110_2$, $110_3$, $110_4$, and $110_5$ differ essentially in the embodiment of the movable portion or part 122 for locking the ends 28e and 28f of the braid 28.

The movable part 122 of the spacer $110_1$ is mounted in a housing 124 made in the body of the spacer 120 and opening out into its bottom face 120a. The movable part 122 presents a sloping top face 126 that co-operates with the sloping top face 128 of the housing 124. By the face 126 sliding against the face 128, the end 130 of the movable part 122 can be moved towards the front wall 132 of the housing 124. The spacer body 120 also has two slots 134 and 136 for passing the braid 28 that can thus penetrate into the inside of the housing 124. The front face 130 of the movable portion 122 defines two clamping surfaces 130a and 130b that co-operate with clamping faces 132a and 132b defined by the front wall 132 of the cavity 124. Since the braid 28 is disposed between these two pairs of clamping surfaces, movable the movable portion 122 towards the face 132 of the cavity 124 of the spacer body serves to clamp two portions of the braid 28 close to their free ends 28e and 28f. In FIG. 10A, it can be seen that the front wall 132 of the cavity 124 is provided with a slot 139 that enables the ends 28e and 28f of the braid 28 to pass through after the braid portions have been passed between the clamping faces 130a, 132a, 130b, 132b.

The movable portion 122 is preferably moved relative to the stationary body 120 with the help of a screw 138 having its threaded portion 138a co-operating with a tapped bore 142 formed in the movable portion 122. In addition, the head 138b of the screw 138 is held pressed against the top face 120b of the body 120 of the spacer. It will be understood that by turning the screw 138 in one direction or the other, it is possible to move the movable portion 122 in one direction or the other. The spacer body 120 also has a passage 140 for a portion of the braid 28, through which portion the braid can slide freely.

FIGS. 11, 12A, 12B, and 12C show a second embodiment of the spacer provided with the securing mechanism, this spacer being referenced $110_2$.

This second embodiment of the spacer $110_2$ is very similar to that shown in FIGS. 9 and 10. The spacer body 150 constitutes the stationary portion of the securing mechanism and the part 152 constitutes the movable portion. The spacer body 150 is provided with a cavity 154 presenting a sloping end wall 156 and an inside front wall 158. The cavity 154 opens out into the top face 150a of the body 150. The movable part 152 has a bottom face 160 that can slide against the sloping end wall 156 of the cavity 154.

As in the above embodiment, the spacer body 150 has two side slots 162 and 164 for passing the braid 28, and an axial slot 166 for passing the ends 28e and 28f of the braid 28. The inside front face of the cavity 154 defines two clamping surfaces 154a and 154b. The movable part 152 presents a front face 168 that itself defines two clamping surfaces 168a and 168b suitable for co-operating with the clamping surfaces 154a and 154b of the spacer body 150.

As in the above embodiment, by moving the movable part 152 in the cavity 154 relative to the stationary part 150, the pairs of clamping surfaces 154a & 168a, and 154b & 168b are moved towards or away from each other. This movement is preferably obtained with the help of a screw 170 whose head 172 bears against the top face 152a of the movable part 152 and whose threaded portion 174 passes freely through an oblong bore 176 formed in the movable part 152, and co-operates with tapping 178 formed in the end wall of the spacer body 150. By turning the screw 170, with its head 172 bearing against the top face 152a of the movable part 152, the movable part 152 is caused to move relative to the stationary part 150, thereby securing the braid 28 to the spacer $110_2$.

With reference to FIGS. 13A to 13C, there follows a description of a third embodiment of the spacer fitted with the securing mechanism, which spacer is given reference $110_3$. Like the other spacers $110_1$, and $110_2$, the spacer $110_3$ comprises a body 180 that constitutes the stationary portion of the securing mechanism together with a movable part 182 that is mounted to slide in a cavity 184 formed in the body of the spacer body 180 and opening out into the proximal face 180a of the spacer body 180. The cavity 184 has a substantially horizontal end wall 186 on which the likewise substantially horizontal end wall 188 of the movable part 182 can slide. The movable part 182 has an axial channel 190 and two flanges 192 and 194.

As shown better in FIG. 13C, the end wall 196 of the axial channel 190 in the movable part 182 has a portion 196a that is substantially horizontal and a portion 196b that is inclined. The flanges 192 and 194 of the movable part 188 are provided with respective free passages 198 and 200 for passing portions of the braid 28 that extend parallel to the movement direction of the movable part 182. The spacer body 180 includes in its top face 180b a tapped bore 202 suitable for cooperating with a screw 204. The bore 202 opens out into the housing 184. The spacer body 180 also has two side slots 206 for passing portions of the braid 28, as shown more clearly in FIG. 13A. Its distal end 208 presents a free passage 210 for the braid 28, as shown more clearly in FIG. 13A. A portion of the braid 28 penetrates into the housing 184 via the side slots 206 and passes through the slots 198 and 200 of the movable part 188 so that the free ends 28e and 28f of the braid 28 exit from the movable part 188, as shown more clearly in FIG. 13A. The distal faces 192a and 194a of the flanges 192 and 194 of the movable part 182 constitute clamping faces suitable for co-operating with the distal vertical face 184a of the housing 184.

As shown more clearly in FIG. 13C, the bottom end 204a of the screw 204 co-operates with the inclined portion 196b of the end wall 196 of the channel 190 in the movable part 188.

Thus, by turning the screw 204, it is possible to move the movable part 188 in one direction or the other relative to the wedge body 180. This serves to clamp portions of the braid 28 between the clamping face 184a of the stationary portion 180 and the clamping faces 192a and 194a of the movable part 188.

Figure 14A:
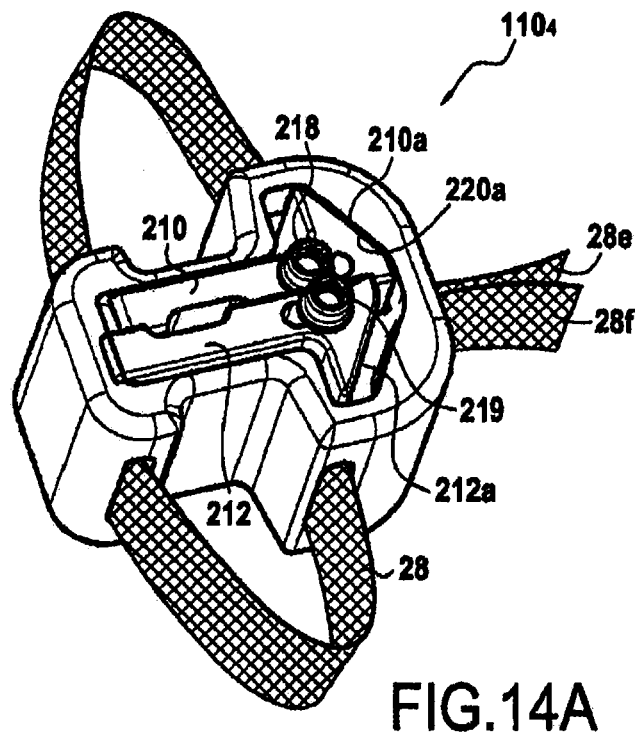
FIG. 14A is a perspective view of a fourth embodiment of a spacer with a braid-securing mechanism, suitable for use in the stabilization system of the disclosure.
Figure 14B:
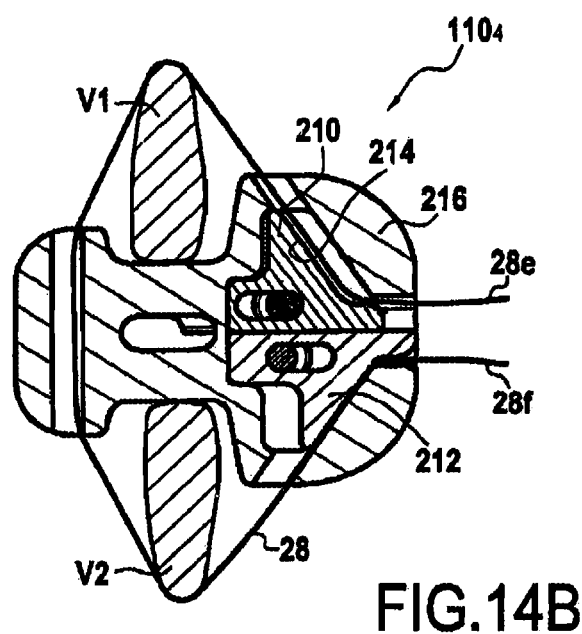
FIG. 14B is a cross-sectional view along the length of the spacer in FIG. 14A, showing a movable part.

The spacer $110_4$ with a clamping system as shown in FIGS. 14A and 14B is very similar to the spacer $110_2$. In this embodiment, the movable part is subdivided into two independent movable parts 210 and 212. These two movable parts 210 and 212 can be moved in translation inside the housing 214 that is formed in the spacer body 216. Each movable half-part 210 and 212 is fitted with a screw 218 and 219 for controlling its movement, each of these screws having exactly the same function as the screw 172 in the spacer $110_2$. The braid 28 is clamped and thus secured to the spacer by co-operation between each of the clamping faces 210a and 212a as defined by the proximal ends of the movable half-parts 210 and 212 and by a common clamping surface 220a defined by a portion of the wall of the housing 214 in the spacer body 216. The advantage of this embodiment is that it enables each end of the braid 28 to be secured separately to the spacer, which makes it possible under certain circumstances to enable the surgeon to perform special adjustment.

Figure 15:
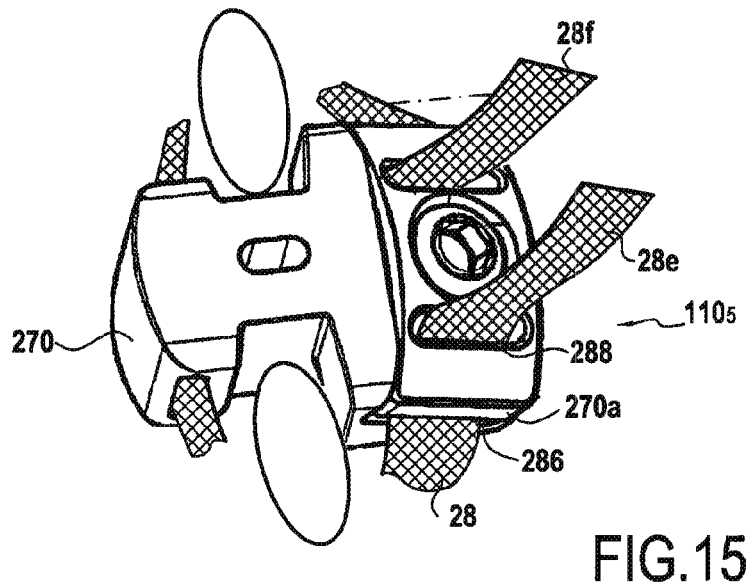
FIG. 15 is a perspective view of a fifth embodiment of a spacer with a securing mechanism.
Figure 16:
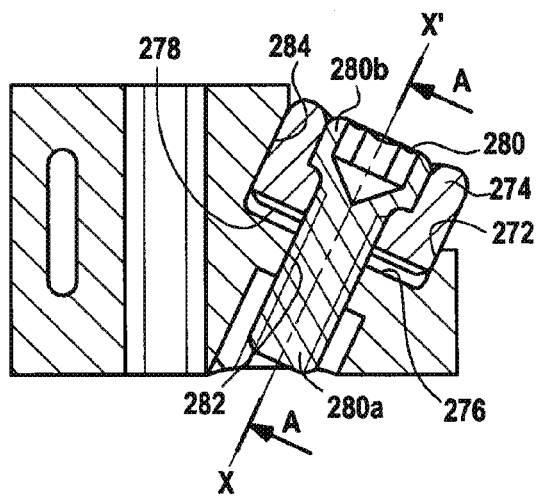
FIG. 16 is a cross-sectional view along the length of the spacer in FIG. 15.
Figure 16A:
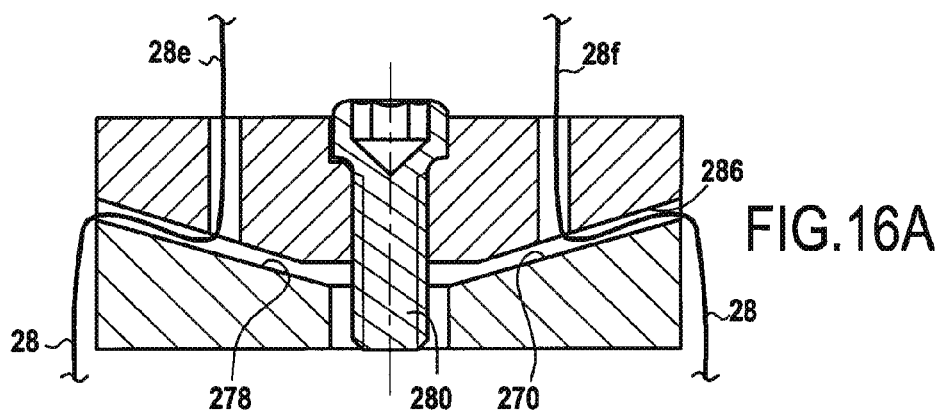
FIG. 16A is a cross-sectional view along the width of the spacer in FIG. 15, showing the securing mechanism.

In FIGS. 15, 16, and 16A, there can be seen a fifth embodiment of a spacer $110_5$ that is provided with a securing mechanism.

In this embodiment, the stationary portion of the securing mechanism is constituted by the spacer body 270. In the proximal portion 270a of the spacer body there is provided a housing 272 for receiving the movable portion 274. The end wall 276 of the housing 272 constitutes a first clamping surface for the portions of the braid 28. The bottom face 278 of the movable part 274 constitutes the second clamping surface. The movable part 274 is moved in translation along the direction XX' by a control screw 280 having a threaded portion 280a that co-operates with tapping 282 formed in the spacer body 270. The head 280b of the screw 280 bears against the bottom of a counterbore 284 formed in the movable part 274.

Portions of the braid 28 penetrate between the clamping surface 276 and 278 via slots 286 formed in the spacer body 270, and the free ends 28e and 28f of the braid 28 exit via slots 288 formed in the movable part 274. By acting on the screw 280, the clamping surfaces 276 and 278 can be moved away from or towards each other.

It should be observed that the above-described securing mechanisms are all of the same general structure. They comprise two parts that are movable relative to each other and between which two portions of the braid close to its free ends 28e and 28f are interposed. A mechanical member, usually a screw, serves to cause the parts to move towards or away from each other. When the two parts are moved towards each other, the two braid portions are secured to each other and to the securing mechanism by being wedged or clamped.

This applies regardless of whether the securing mechanism is independent of the spacer (FIGS. 1 to 6), or whether the securing mechanism is mounted in a spacer (FIGS. 7 to 16).

Figure 17:
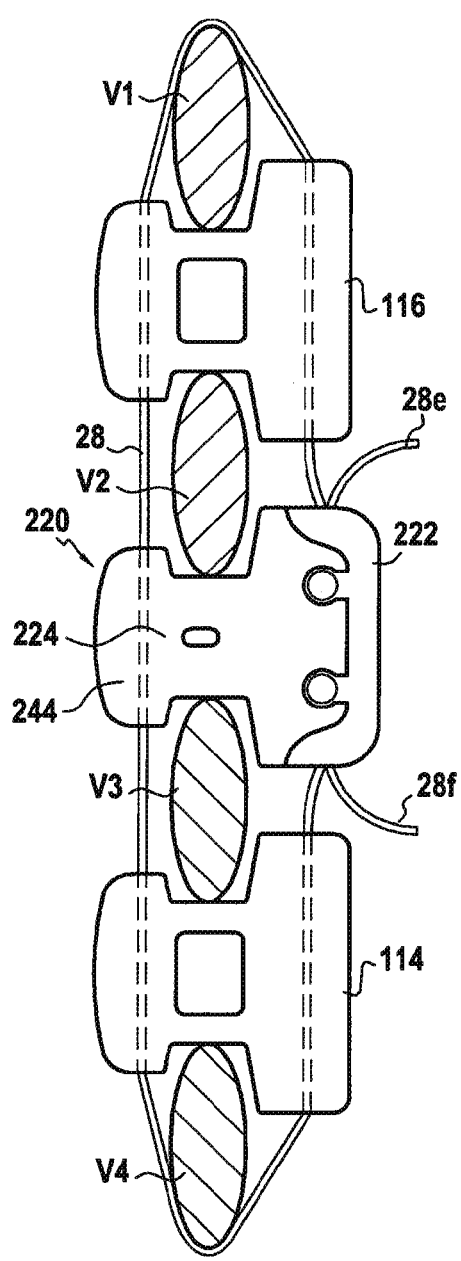
FIG. 17 is an elevation view of an embodiment of the stabilization system for four vertebrae comprising simple spacers and an embodiment of an intervertebral spacer fitted with a braid-securing mechanism.

FIG. 17 shows a first variant of the second embodiment of the stabilization system of the disclosure.

In this variant of the second embodiment of the stabilization system of the disclosure, as shown in FIG. 17, the difference compared with the stabilization system shown in FIG. 8 consists solely in the fact that the spacer 220 provided with a securing mechanism is of a different type. The stabilization system as a whole also comprises simple spacers 114 and 116 interposed between vertebrae V1 and V2 and between vertebrae V3 and V4, and a braid 28 that co-operates with the spacers in exactly the same manner as in FIG. 8.

The spacer 220 differs essentially from the spacers 210 by the fact that the securing mechanism 222 that is associated therewith for securing the braid 28 with this spacer is removable from the body 224 of the spacer 220. More precisely, the securing mechanism is preferably secured of the spacer body 224 by a clip system as described below.

Figure 18A:
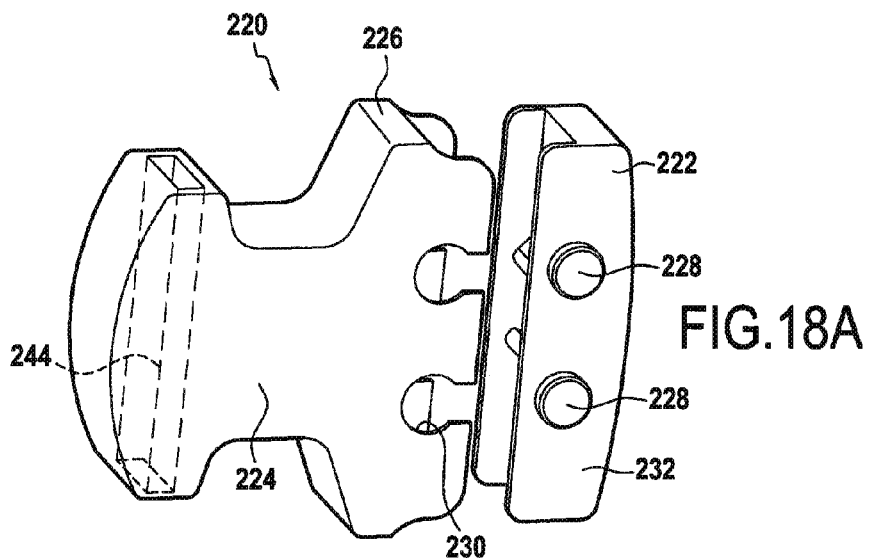
FIGS. 18A and 18B are perspective views of the intervertebral spacer fitted with a braid-securing mechanism shown in FIG. 17.
Figure 18B:
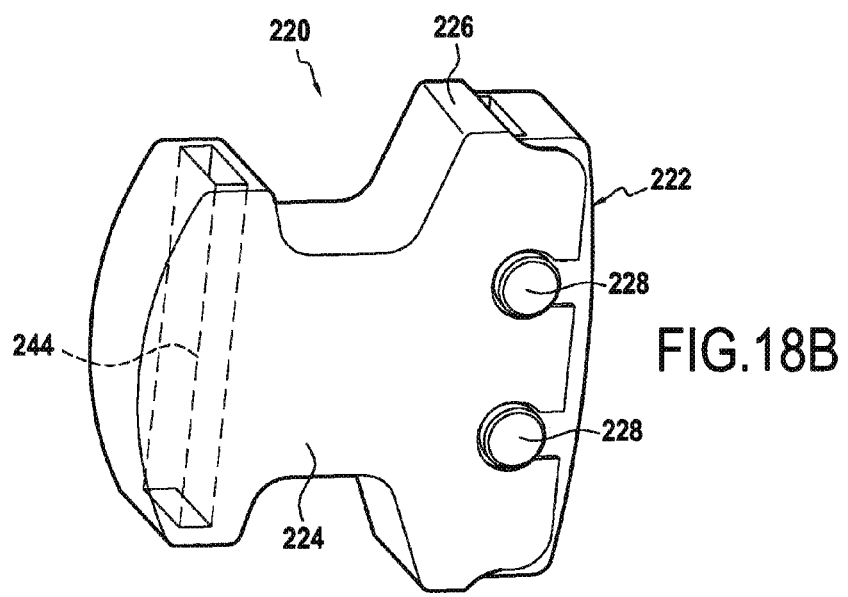
Figure 18C:
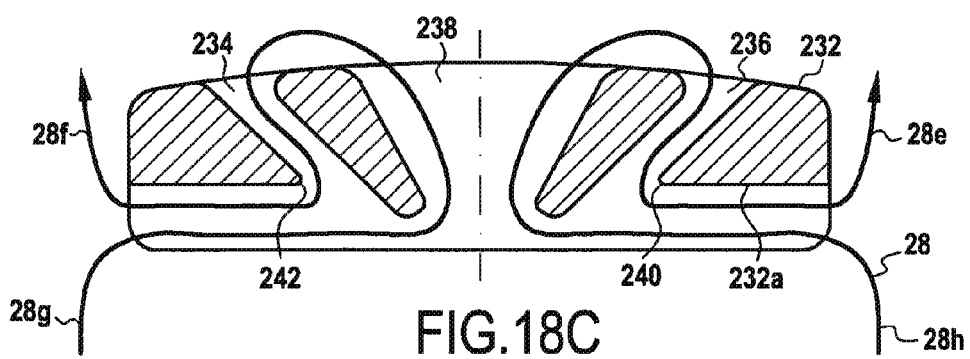
FIG. 18C is a cross-sectional view along the width of the spacer in FIGS. 18A and 18B, showing the braid-securing mechanism.

FIGS. 18A, 18B, and 18C show the spacer 220 and its securing mechanism 222. This spacer, which is preferably suitable for lateral insertion, is described in detail in PCT patent application WO 2007/099258, which is incorporated herein by reference.

The securing mechanism 222 can be fastened to the proximal prong 226 of the spacer body 224 by a clip-fastener system that is constituted, for example, by two studs 228 carried by two side faces of the securing mechanism 222 suitable for co-operating with elastically deformable notches 230 formed in the faces of the proximal prong 226 of the spacer body 224. As shown more clearly in FIGS. 18A-18C, the braid 28 is secured to the spacer 220 by a system of slots made in the body 232 of the securing mechanism 222. This braid-securing mechanism comprising two systems that are self-locking is described in detail in PCT patent application WO 2007/120277, which is incorporated herein by reference. There are two inclined side slots 234 and 236 and an axial slot 238. The side slots 234 and 236 co-operate with the inside face 232a of the body 232 of the securing mechanism 222 to define edges 240 and 242. FIG. 18C shows the path followed by the braid 28 inside the body 232 of the securing mechanism 222. The traction free ends 23e and 28f of the braid are identified as its portions 28g and 28h going towards the simple spacers 114 and 116.

When the securing mechanism 222 has been clipped onto the spacer body 224 and when the surgeon is exerting appropriate traction on the free ends 28e and 28f of the braid using the above-mentioned surgical instrument, the braid becomes wedged in the body 232 of the securing mechanism, in particular because of the presence of the edges 240 and 242. The body 224 of the spacer 220 also has a free passage 244 for a braid portion 28.

Figure 19:
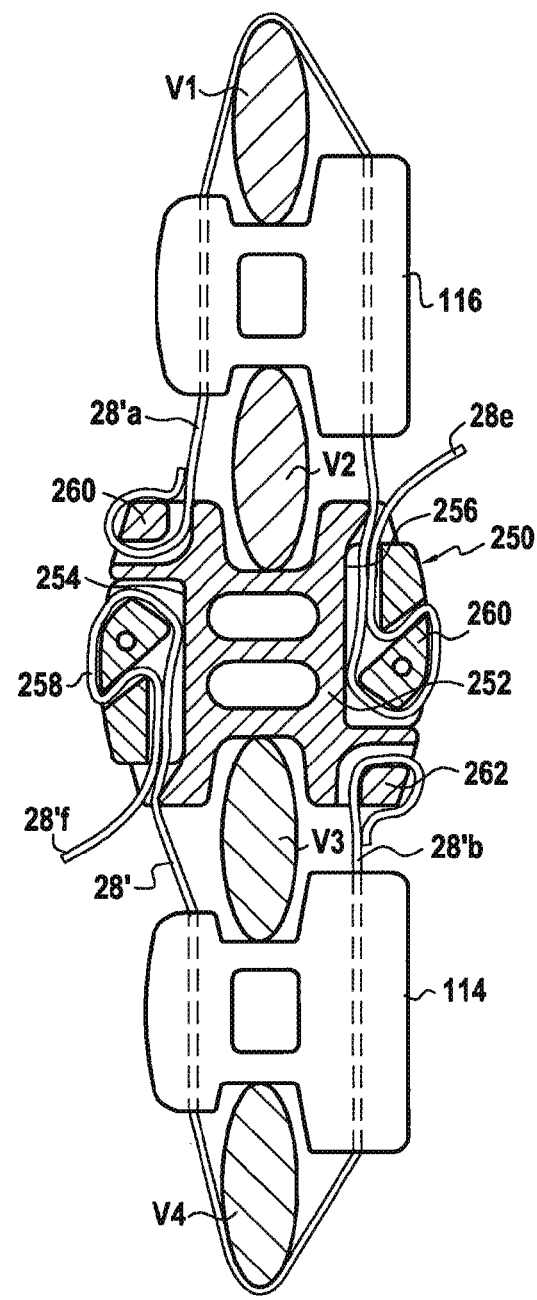
FIG. 19 is an elevation view, partially cross-sectional, showing an embodiment of the system for stabilizing four vertebrae comprising simple spacers and an embodiment of a spacer fitted with a securing mechanism for securing the ends of the braid.

FIG. 19 shows a second variant of the second embodiment of the stabilization system in accordance with the disclosure. This system again comprises a braid 28 and spacers 114 and 116 interposed between the vertebrae V4 and V3 and also between the vertebrae V2 and V1. In this embodiment of the spacer 250, the difference lies in the means for securing the ends of the braid 28. The spacer 250 with its securing mechanisms is described in PCT patent application WO 2002/071960, which is incorporated herein by reference. The spacer 250 comprises a spacer body 252 presenting two side faces 254 and 256. Each of the side faces 254 and 256 can have a locking member 258 or 260 clipped thereto, the set of two locking members forming the braid-securing mechanism. Two braids 28'a and 28'b are used. A first end of each braid is secured to a respective portion 260 or 262 of the spacer body 252. The other free end 28'ae or 28'bf is engaged in a respective one of the locking systems 258 and 260. Each locking system 258 and 260 corresponds to exactly half of the locking system shown in FIG. 18C.

It should be observed that if two distinct braids 28'a and 28'b are used, then the surgeon needs to exert traction on only one braid portion end 28'ae or 28'bf, as in the other embodiments of the disclosure.

It should also be observed that since the locking members are disposed on both side faces of the spacer body the technique of insertion by a lateral approach is not usable.

Finally, in the embodiments shown in FIGS. 17 and 19, the free end of the braid is secured to the securing mechanism by locking the braid because it follows a sinuous path through the securing mechanism, thereby ensuring that it becomes self-blocking by friction when a traction force is exerted on the main portion of the braid.

Figure 20:
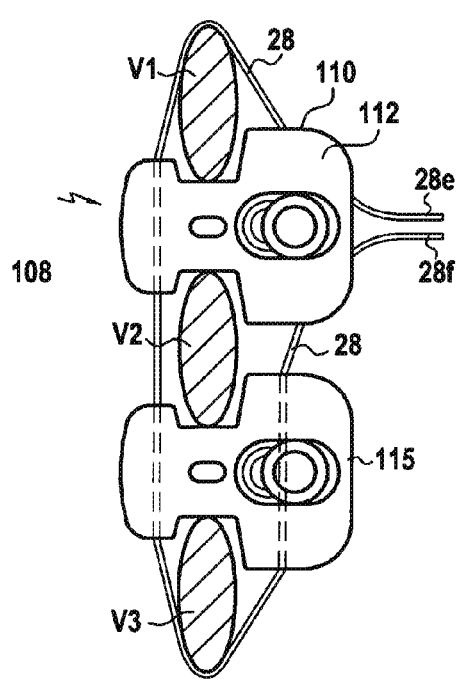
FIG. 20 is an elevation view of a first variant of the stabilization system shown in FIG. 7.
Figure 22:
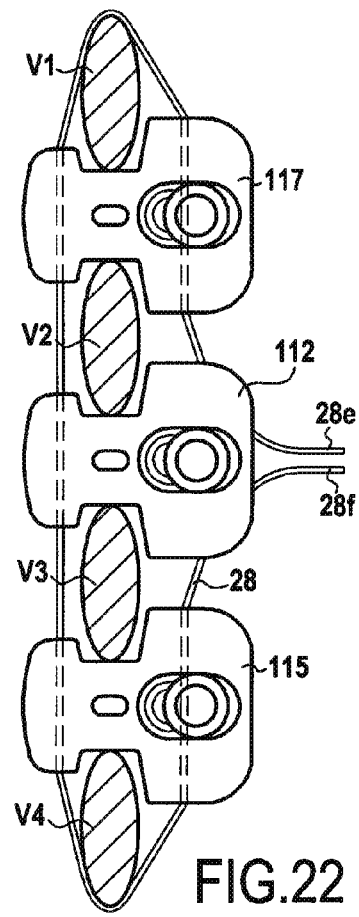
FIG. 22 is an elevation view of a variant of the stabilization system shown in FIG. 8.
Figure 21:
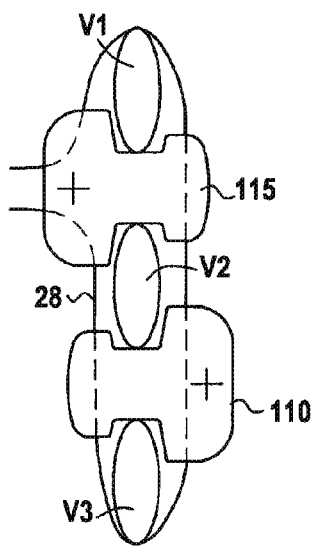
FIG. 21 is an overall view of a second variant of the stabilization system shown in FIG. 7.

FIGS. 20 to 22 show other variants of the second embodiment of the disclosure.

The first variant as shown in FIG. 20 is very similar to the embodiment shown in FIG. 7. The difference lies in the structure of the simple spacer 115. Instead of having solely the function of guiding the braid 28, the spacer 115 also has a function of clamping a portion of the braid 28. The spacer 115 may have the same structure as the spacer 110, but it is used differently. The braid 28 enters via the slot 134 of FIG. 9 and leaves via the analogous second slot. Consequently, the simple spacer 115 not only performs a guidance function, but it also performs a function of clamping a portion of the braid 28 by acting on the movable part 122 relative to the stationary portion 120. In contrast, the simple spacer 115 does not under any circumstances serve to secure the free ends of the braid 28, which function is performed by the spacer 110.

FIG. 21 shows a variant of FIG. 20 that differs therefrom by the fact that the spacers 110 and 115 are inserted between the spinous processes of the vertebrae V1, V2, and V3 using different approaches.

In FIG. 22, there is shown another variant of the second embodiment of the disclosure. In this variant, there are two simple spacers 115 and 117 having functions of clamping portions of the braid 28. It is possible to use stabilization systems comprising a spacer 112 provided with a securing mechanism for the free ends of the braid 28, at least one simple spacer such as the spacer 114 shown in FIG. 17 that serves solely to guide the braid 28, and at least one simple spacer of the same type as the spacer 115 that has a function of clamping a portion of the braid.

Figure 23:
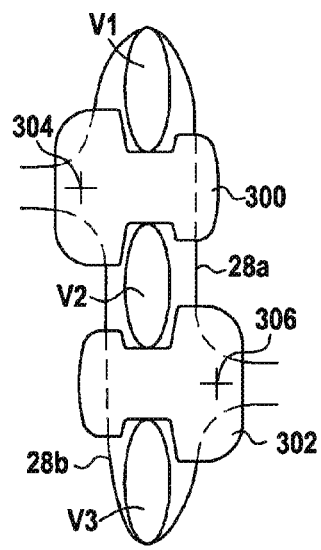
FIGS. 23 and 24 show two other embodiments of the stabilization system.
Figure 24:
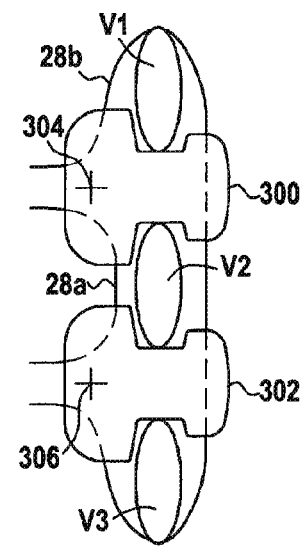

FIGS. 23 and 24 show another variant of the second embodiment of the disclosure. In this variant, the stabilization system comprises two braids 28a and 28b and two spacers 300 and 302, each provided with a system 304 and 308, each of which is physically suitable for securing to one end of each of the braids 28a and 28b. It should be understood that one of the spacers 300 or 302 serves for securing the two braids 28a and 28b, while the other spacer serves for securing the free end of each braid after the surgeon has exerted an appropriate amount of traction on the free ends of the braid exiting one of the spacers 300, 302.

This solution makes it possible, as a function of ease of access, to exert traction on the braid via one or the other of the spacers 300 and 302 or to begin by exerting traction on the free ends of the braid via one of the spacers and to finish off applying traction to the braids via the other spacer.

What is claimed is:

1. A system for stabilizing at least three vertebrae each having a spinous process, the system comprising:
   a flexible braid having first and second free ends and intermediate portions therebetween defining a length, said length of said flexible braid configured to form a single loop around the spinous processes of said at least three vertebrae;
   a first spacer configured to be interposed between the spinous processes of first and second adjacent vertebrae of the at least three vertebrae and having means for guiding first and second intermediate portions of the flexible braid, the guiding means comprising a first internal passage and a second internal passage, the first internal passage extending through the first spacer in a superior-inferior direction and located entirely on a first side of a median plane of the first spacer aligned with a median plane of the at least three vertebrae, the second internal passage extending through the first spacer in a superior-inferior direction and located entirely on a second side of the median plane of the first spacer aligned with the median plane of the at least three vertebrae, said first and second intermediate portions of the flexible braid passing, respectively, freely through the first and second internal passages with a portion of said flexible braid between the two intermediate portions positionable around the spinous process of the first vertebrae; and
   a second spacer configured to be interposed between the spinous processes of the second and third adjacent vertebrae of the at least three vertebrae, the second spacer including a braid-securing system through which the two free ends of the braid can be inserted and pulled, the braid-securing system allowing said free ends to be secured to the second spacer, with a third intermediate portion of the flexible braid between the first intermediate portion and the first free end extending from the first spacer to the braid-securing system of the second spacer, and a fourth intermediate portion of the flexible braid between the second intermediate portion and the second free end positionable around the third vertebra and extending from the first spacer to the braid-securing system of the second spacer.

2. The stabilization system according claim 1, wherein said braid-securing system is removably mounted on the second spacer.

3. The stabilization system according claim 1, wherein said braid-securing system forms an integral portion of the second spacer.

4. The stabilization system according claim 3, wherein said braid-securing system is suitable for securing said two free ends of the flexible braid together.

5. The stabilization system according claim 3, wherein said braid-securing system includes removable fastener members on a body of the second spacer.

6. The stabilization system according claim 3, wherein a body of the second spacer has two side faces, and wherein said braid-securing system is secured to one of said two side faces.

7. The stabilization system according claim 3, wherein said flexible braid comprises two braid portions, each having a free end and a secure end, wherein said free end is one of said first and second free ends of said flexible braid, wherein a body of said second spacer comprises first and second side faces, wherein said braid-securing system comprises a first securing member secured to said first side face and a second securing member secured to said second side face, and wherein said secure end of each braid portion is permanently secured to said body of said second spacer and said free end of each braid portion is retractably secured to one of said first and second securing members.

8. The stabilization system according to claim 1, wherein said braid-securing system comprises a mechanical member and two portions that are movable relative to each other, wherein said braid-securing system is constructed to allow portions of said flexible braid that are close to said first and second free ends be placed between said two movable portions of said braid-securing system, and wherein said mechanical member is constructed for causing said two movable portions of said braid-securing system to move towards each other, whereby said first and second free ends of the flexible braid are secured to said braid-securing system.

9. The stabilization system according claim 1, wherein the second spacer has guiding means for guiding the fourth intermediate portion of the braid.

10. The stabilization system according to claim 9, wherein said guiding means of the second spacer comprises an internal passage extending through the second spacer in a superior-inferior direction and located on a side opposite of the braid-securing system, said fourth intermediate portion passing freely through said internal passage of said second spacer.

* * * * *